US00PP31260P2

(12) United States Plant Patent
Werner

(10) Patent No.: US PP31,260 P2
(45) Date of Patent: Dec. 24, 2019

(54) ***CERCIS* PLANT NAMED 'NC2016-2'**

(50) Latin Name: *Cercis canadensis*
Varietal Denomination: NC2016-2

(71) Applicant: North Carolina State University, Raleigh, NC (US)

(72) Inventor: Dennis James Werner, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 16/350,659

(22) Filed: Dec. 18, 2018

(51) Int. Cl.
*A01H 6/00* (2018.01)
*A01H 5/02* (2018.01)

(52) U.S. Cl.
USPC ..... Plt./216

(58) Field of Classification Search
USPC ..... Plt./216
CPC ..... A01H 6/00; A01H 5/02
See application file for complete search history.

(56) References Cited

U.S. PATENT DOCUMENTS

PP21,451 P3 11/2010 Jackson et al.

*Primary Examiner* — Keith O. Robinson
(74) *Attorney, Agent, or Firm* — Buchanan Ingersoll & Rooney PC

(57) ABSTRACT

A new and distinct variety of *Cercis canadensis* eastern redbud plant, herein referred to by its cultivar name, 'NC2016-2', is provided which forms emerging purple colored foliage that matures to gold colored foliage. The new variety provides vegetation that is moderately vigorous and the growth habit is semi-weeping. The new variety is well suited for providing attractive ornamentation in the landscape.

3 Drawing Sheets

Botanical/commercial classification:
Latin name—*Cercis canadensis.*
Common name—eastern redbud.
Varietal denomination: 'NC2016-2'.

SUMMARY OF THE INVENTION

The new variety of *Cercis canadensis* eastern redbud plant was selected from a population of second generation decedents from a hybrid cross. The controlled hybrid cross occurred during March, 2010 at Raleigh, N.C., U.S.A., wherein two parents were crossed which previously had been studied in the hope that they would contribute the desired characteristics. The female parent (i.e., the seed parent) was an unnamed seedling (not patented). The male parent (i.e., the pollen parent) was the 'JN2' variety (U.S. Plant Pat. No. 21,451).

The parentage of the new variety can be summarized as follows:

unnamed seedling x 'JN2'

The new cultivar was discovered and selected as a single flowering plant within the second generation progeny of the above-stated hybrid cross. Selective study resulted in the identification of a single plant of the new variety in 2017 at Jackson Springs, N.C.

It was found that the new variety of *Cercis* plant of the present invention possesses the following combination of characteristics:

(a) forms attractive, foliage which emerges purple colored and matures to gold colored;
(b) exhibits semi-weeping growth habit; and
(c) provides moderately vigorous vegetation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the unnamed seedling female parent (i.e., the seed parent) displays weeping growth habit with purple colored foliage and the 'JN2' variety (i.e., the pollen parent) displays a non-weeping growth habit with foliage that changes from golden orange to speckled lime as it matures, whereas the new variety displays emerging purple-colored foliage that matures to gold colored foliage and semi-weeping growth habit.

The new variety has been found to undergo asexual propagation at Belvidere, Tenn. by chip budding since 2016. Asexual propagation by chip budding in Belvidere, Tenn. has shown that the characteristics of the new variety are stable and are strictly transmissible by such asexual propagation from one generation to another. Accordingly, the new variety undergoes asexual propagation in a true-to-type manner.

The new variety has been named 'NC2016-2'.

BRIEF DESCRIPTION OF THE PHOTOGRAPHS

The accompanying photographs shows as nearly true as it is reasonably possible to make the same, in color illustrations of this character, typical specimens of the new variety. The *Cercis* plants of the new variety were approximately two years of age and were observed at Jackson Spring, N.C., U.S.A. while growing outdoors.

Figure 1:
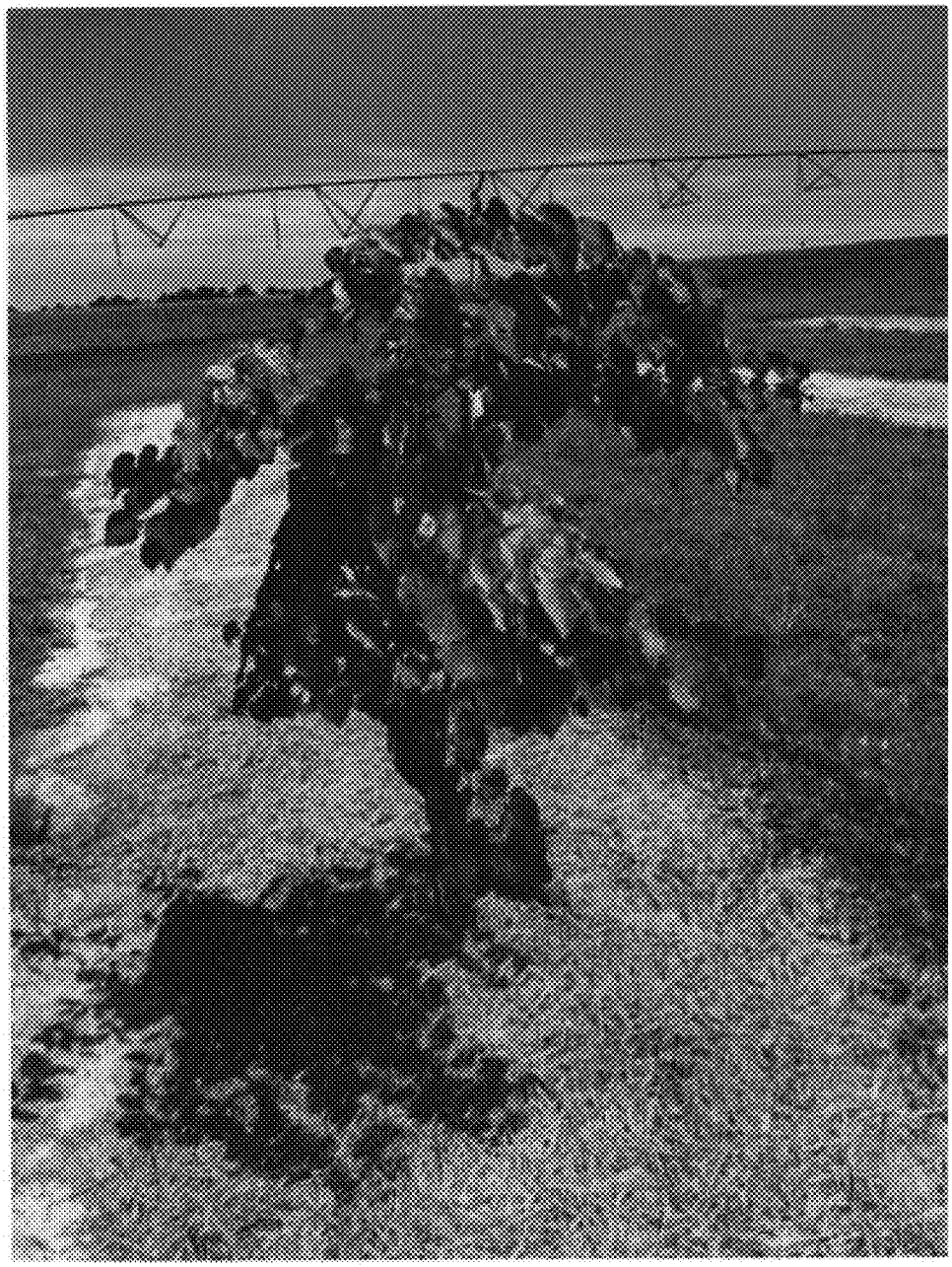
Figure 2:
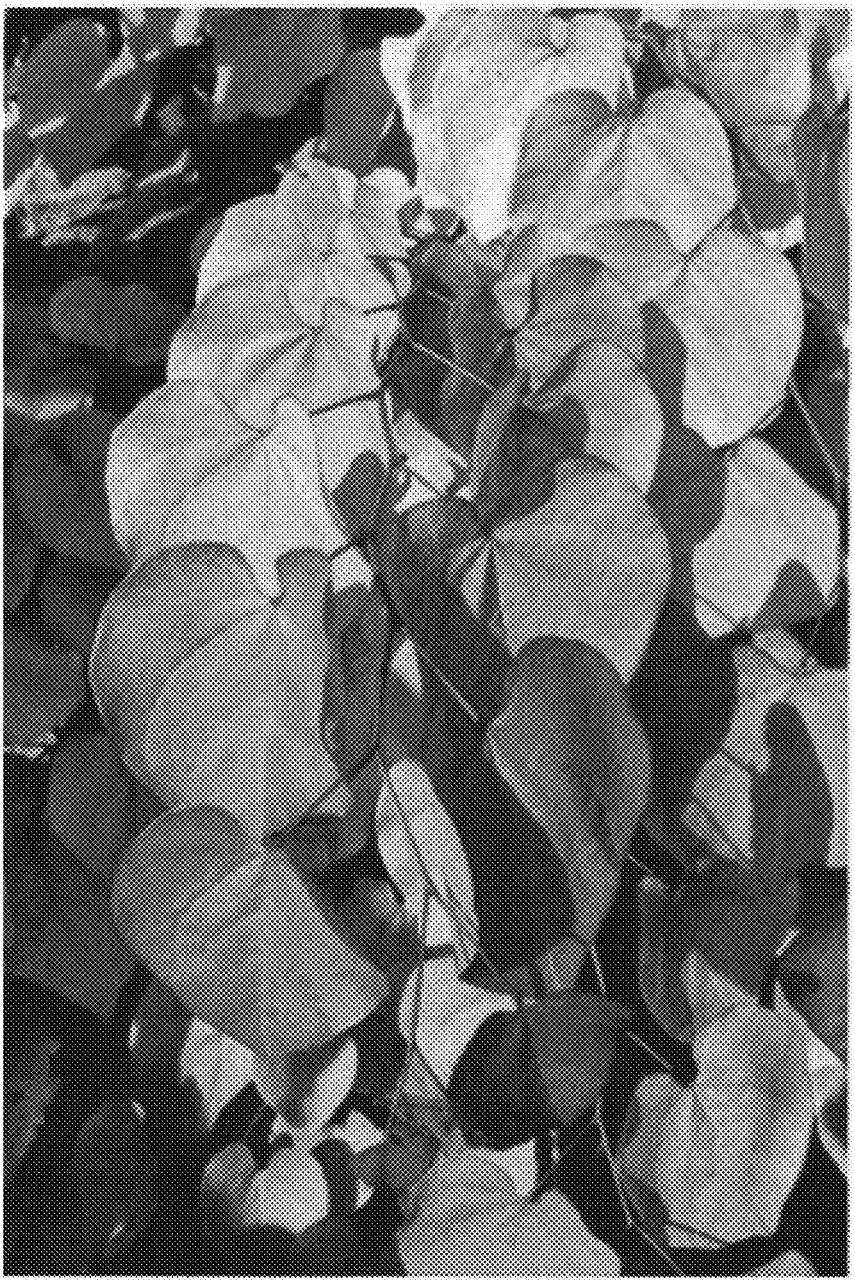
Figure 3:
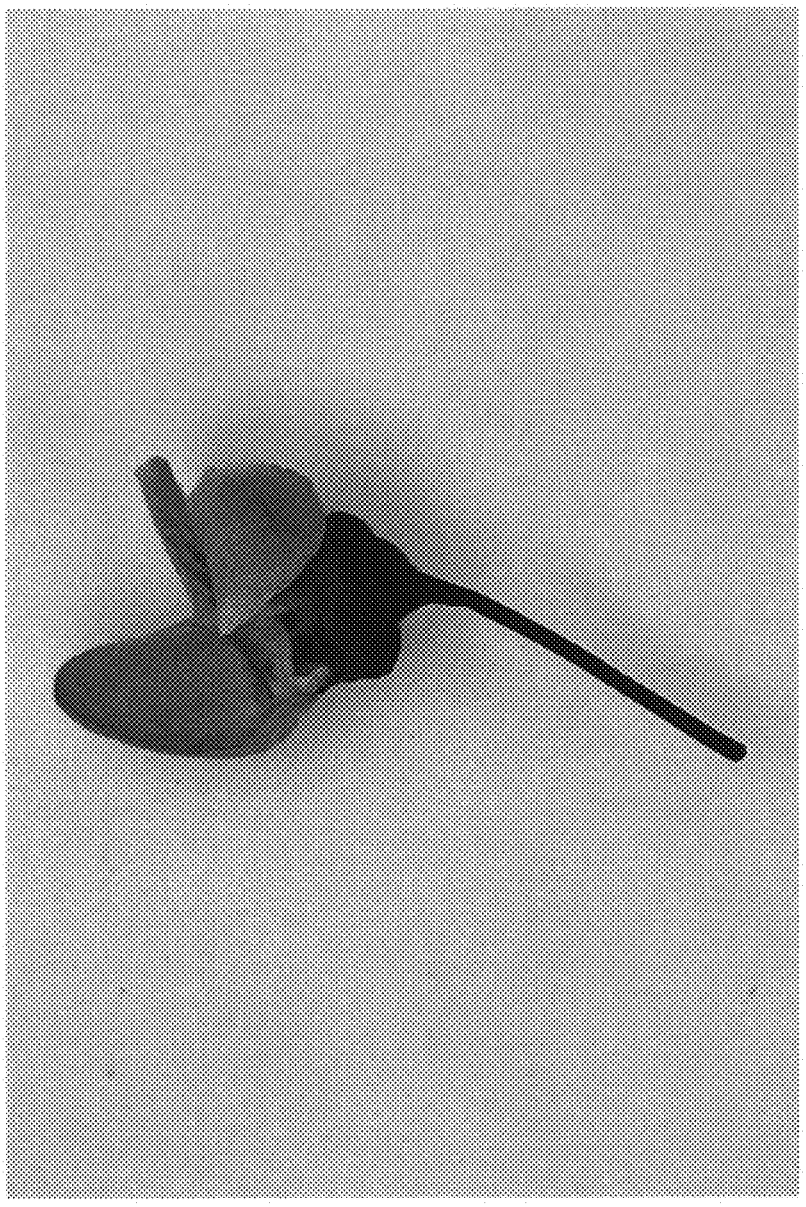

FIG. 1—illustrates a specimen the tree—side view.
FIG. 2—illustrates a specimen of the foliage—close view.
FIG. 3—illustrates a specimen of a flower—close view.

DETAILED BOTANICAL DESCRIPTION

The chart used in the identification of colors described herein is The Royal Horticultural Society ("R.H.S." Colour Chart), London, England, 2015 edition. The terminology which precedes reference to the chart has been added to indicate the corresponding color in more common terms. The color values of the flowers were determined in April 2019 and the color values of the foliage were determined in June 2019 under natural light conditions in Cochranville, Pa.

The following descriptions and measurements describe plants produced from chip budding and grown outside in a test field in Cochranville, Pa. Plants were approximately three years of age. Measurements and numerical values represent averages of typical plants.

Class: *Cercis* Plant.

Plant:

*Growth habit*.—Semi-weeping.

*Type*.—Deciduous perennial tree.

*General appearance*.—Moderately vigorous.

*Size*.—Height: approximately 2.13 meters. — width: approximately 1.3 m.

*Trunk*.—Diameter immediately above graft union: approximately 4.8 cm. — texture: slightly rugose.

*Branches*.—Generally: highly branched. — strength: moderately strong. — diameter of new growth: approximately 2.0 mm. — diameter of one-year old growth: approximately 3.4 mm. — texture of new growth: glabrous. — color of young stem: commonly near Greyed-Purple Group N186C. — color of mature stem: commonly near Greyed-Purple Group 187B. — lenticel: numerous, tiny; length is less than 1.0 mm on average; shape is elliptic; color is commonly near Grey-Brown Group N199B.

Foliage:

*Color*.—Emerges purple and matures to gold.

*General description*.—Type: deciduous. — arrangement: alternate.

*Leaves*.—Shape: cordate. — apex: acute. — base: cordate. — margin: entire. — length: approximately 11.0 cm. — width: approximately 10.0 cm. — texture of upper and lower surfaces: smooth, glabrous. — venation pattern: palmate. — color of upper surface of mature foliage: commonly near Yellow-Green Group N144A with venation of near Yellow-Green Group N144B. — color of lower surface of mature foliage: commonly near Greyed-Purple Group 186B with venation of near Greyed-Purple Group 186A. — color of upper and lower surfaces of young foliage: commonly near Greyed-Purple Group 187A with indistinguishable venation. — fragrance: none detected.

*Petiole*.—Length: approximately 4.0 cm. — diameter: approximately 1.1 mm. — texture: smooth, glabrous. — color: commonly near Greyed-Purple Group N186C.

Flowering description:

*Flowering season*.—Flowers in early spring.

*General description*.—Compound corymbs. — aspect: facing upward to slightly outward. — fragrance: slightly sweet. — quantity per plant: approximately 150-180. — diameter: approximately 5.0 cm to 10.0 cm. — height: approximately 2.5 cm.

*Peduncle*.—Strength: strong. — shape: rounded. — aspect: erect to about 45° from branch axis. — length: approximately 1.0 cm. — diameter: approximately 0.2 cm. — texture: glabrous. — color: commonly near Greyed-Purple Group 187B.

Flower description:

*General description*.—Type: single, rotate, not persistent. — aspect: upright. — quantity per inflorescence: approximately 5 to 12 per cluster.

*Bud just before opening shape*.—Ovate tapering to a point. — diameter: approximately 4.0 mm. — length: approximately 1.0 cm. — color: commonly near Red-Purple Group 71C. — texture: glabrous.

*Corolla*.—Diameter approximately 1.0 cm. — depth: approximately 7.0 mm.

*Petals*.—Quantity: 5, unfused. — shape: orbicular. — margin: entire. — apex: rounded. — base: obtuse. — length: approximately 7.0 mm. — width: approximately 4.0 mm. — texture of upper and lower surfaces: glabrous. — color of upper and lower surfaces when first and fully open: commonly between Red-Purple Group 64B and 64C.

*Calyx*.—Shape: vase-shaped; 5 rounded lobes at terminus. — diameter: approximately 4.0 mm at top of hypanthium. — length: approximately 4.0 mm. — color of outer and inner surfaces: commonly near Red-Purple Group 59B. — texture of inner and outer surfaces: glabrous.

*Sepals*.—Quantity: 5, attached to top of hypanthium. — arrangement: in a single whorl.

*Pedicel*.—Strength: strong. — shape: round. — length: approximately 4.0 mm. — diameter: less than 1.0 mm. — texture: glabrous. — color: commonly near Red-Purple Group 59A.

*Reproductive organs*.—Androecium: — Stamen quantity per flower: 10 on average, unfused and attached to apex of hypanthium. — Stamen length: approximately 1.0 mm. — Filament: length is approximately 9.0 mm; color is commonly near Red-Purple Group 68A. — Anther: shape is round to slightly oblong; length is less than 1.0 mm; width is less than 1.0 mm; color is commonly near Red-Purple Group 60A. — Pollen: amount is abundant; color is commonly near Greyed-Yellow Group 162B. — Gynoecium: — Pistil: quantity is 1 per flower; length is approximately 1.0 mm on average; width is less than 1.0 mm; color is commonly near Red-Purple Group 59B; texture is glabrous. — Stigma: shape is round; color is commonly near Yellow-White Group 158A; length is less than 1.0 mm; width is less than 1.0 mm. — Style: shape is elongate; width is less than 1.0 mm; color is commonly near Red-Purple Group 59B. — Ovary: position is superior; shape is round; width is less than 1.0 mm; color is commonly near Red-Purple Group 59B.

*Seed production*.—None observed to date.

Development:

*Vegetation*.—Moderately vigorous.

*Disease and pest resistance*.—Plants of the new variety have not been noted to be resistant to pathogens and pests common to *Cercis* plants.

*Commercial crop time*.—Approximately 1.5 years from budding to finish as a 4 to 6-foot tree.

The new 'NC2016-2' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of *Cercis* plant characterized by the following combination of characteristics:

(a) forms attractive, foliage which emerges purple colored and matures to gold colored;

(b) exhibits semi-weeping growth habit; and (c) provides moderately vigorous vegetation;

substantially as herein shown and described.

* * * * *